(12) United States Patent
Hoffmeier et al.

(10) Patent No.: US 7,311,687 B2
(45) Date of Patent: Dec. 25, 2007

(54) OSTEOARTHRITIS BRACE

(75) Inventors: Carl Hoffmeier, Solana Beach, CA (US); Jennifer Sullivan, San Pedro, CA (US); John Martin, Oceanside, CA (US); Colin Seth Gregersen, Cardiff by the Sea, CA (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 11/098,158

(22) Filed: Apr. 4, 2005

(65) Prior Publication Data

US 2005/0240135 A1    Oct. 27, 2005

Related U.S. Application Data

(60) Provisional application No. 60/564,563, filed on Apr. 21, 2004.

(51) Int. Cl.
*A61F 5/00* (2006.01)

(52) U.S. Cl. .............................. 602/26; 602/16; 602/25

(58) Field of Classification Search .................. 602/26, 602/27–29, 5, 16, 20, 23–25; 128/882
See application file for complete search history.

(56) References Cited

U.S. PATENT DOCUMENTS

| | | | |
|---|---|---|---|
| 2,467,907 A | 4/1949 | Peckham |
| 2,531,074 A | 11/1950 | Miller |
| 3,350,719 A | 11/1967 | McClure, Jr. |
| 3,575,166 A | 4/1971 | Roseman et al. |
| 3,581,741 A | 6/1971 | Roseman et al. |
| 3,669,105 A | 6/1972 | Castiglia |
| 3,902,482 A | 9/1975 | Taylor |
| 3,945,047 A | 3/1976 | Jarrell |
| 3,955,565 A | 5/1976 | Johnson |
| 3,958,569 A | 5/1976 | Vosburgh |
| 4,201,203 A | 5/1980 | Applegate |
| 4,219,892 A | 9/1980 | Rigdon |
| 4,280,489 A | 7/1981 | Johnson |
| 4,287,920 A | 9/1981 | Johnson |

(Continued)

FOREIGN PATENT DOCUMENTS

DE            846895            7/1949

(Continued)

OTHER PUBLICATIONS

Breg, X2K CounterForce, brochure, 2 pages, 2002.

(Continued)

*Primary Examiner*—Justine R. Yu
*Assistant Examiner*—Shumaya Ali
(74) *Attorney, Agent, or Firm*—Knobbe, Martens, Olson & Bear, LLP

(57) ABSTRACT

An osteoarthritis brace having relatively large semi-rigid cuffs for abutting the wearer's thigh and calf. In one embodiment, the semi-rigid cuffs are secured to rigid cuffs of the brace only on one side and in substantially a center of the rigid cuffs. The semi-rigid cuffs bear reaction forces created by a medial/lateral force applied to the wearer's knee by a hinge of the brace. The semi-rigid cuffs provide flesh containment, distribute loads over a large portion of the wearer's flesh, eliminate pinch points and provide enhanced fitting capabilities.

13 Claims, 5 Drawing Sheets

U.S. PATENT DOCUMENTS

| | | | |
|---|---|---|---|
| 4,361,142 A | 11/1982 | Lewis et al. | |
| 4,372,298 A | * 2/1983 | Lerman | 602/26 |
| 4,381,768 A | 5/1983 | Erichsen et al. | |
| 4,428,369 A | * 1/1984 | Peckham et al. | 602/16 |
| 4,506,661 A | 3/1985 | Foster | |
| 4,531,515 A | 7/1985 | Rolfes | |
| 4,567,887 A | 2/1986 | Couch | |
| 4,572,170 A | 2/1986 | Cronk et al. | |
| 4,624,247 A | 11/1986 | Ford | |
| 4,628,954 A | 12/1986 | Dayus | |
| 4,632,098 A | 12/1986 | Grundei | |
| 4,634,176 A | 1/1987 | Scott | |
| 4,643,176 A | 2/1987 | Mason et al. | |
| 4,667,672 A | 5/1987 | Romanowski | |
| 4,703,750 A | 11/1987 | Sebastian | |
| 4,768,500 A | 9/1988 | Mason et al. | |
| 4,796,610 A | 1/1989 | Cromartie | |
| 4,805,606 A | 2/1989 | McDavid | |
| 4,821,707 A | 4/1989 | Audette | |
| 4,854,308 A | 8/1989 | Drillio | |
| 4,856,501 A | * 8/1989 | Castillo et al. | 602/16 |
| 4,870,956 A | 10/1989 | Fatool | |
| 4,872,448 A | 10/1989 | Johnson | |
| 4,886,054 A | * 12/1989 | Castillo et al. | 602/26 |
| 4,938,207 A | 7/1990 | Vargo | |
| 4,940,045 A | 7/1990 | Cromartie | |
| 4,982,732 A | 1/1991 | Morris | |
| 4,999,932 A | 3/1991 | Grim | |
| 5,002,045 A | 3/1991 | Spademan | |
| 5,022,391 A | 6/1991 | Weidenburner | |
| 5,025,575 A | 6/1991 | Lakic | |
| 5,025,782 A | 6/1991 | Salerno | |
| 5,042,464 A | 8/1991 | Skwor | |
| 5,078,128 A | 1/1992 | Grim | |
| 5,085,210 A | 2/1992 | Smith, III | |
| 5,088,478 A | 2/1992 | Grim | |
| 5,107,823 A | 4/1992 | Fratesi | |
| 5,113,599 A | 5/1992 | Cohen | |
| 5,125,400 A | 6/1992 | Johnson | |
| 5,158,767 A | 10/1992 | Cohen | |
| 5,186,163 A | 2/1993 | Dye | |
| 5,207,637 A | 5/1993 | Janke | |
| 5,230,695 A | 7/1993 | Silver | |
| 5,277,697 A | 1/1994 | France et al. | |
| 5,277,698 A | 1/1994 | Taylor | |
| 5,383,844 A | 1/1995 | Munoz et al. | |
| 5,383,845 A | 1/1995 | Nebolon | |
| 5,385,534 A | 1/1995 | Cassford | |
| D357,070 S | * 4/1995 | Castillo | D24/190 |
| 5,407,420 A | 4/1995 | Bastyr et al. | |
| 5,458,565 A | 10/1995 | Tillinghast et al. | |
| 5,766,140 A | 6/1998 | Tillinghast et al. | |
| 5,807,294 A | * 9/1998 | Cawley et al. | 602/26 |
| RE37,297 E | * 7/2001 | Smith, III | 602/26 |

FOREIGN PATENT DOCUMENTS

| | | |
|---|---|---|
| DE | 1 024 204 | 2/1958 |
| DE | 3825813 | 7/1988 |
| DE | 195 06 912 A1 | 9/1995 |
| FR | 2627381 | 8/1989 |
| GB | 2136294 | 9/1984 |
| WO | WO 2004/002376 A1 | 1/2004 |

OTHER PUBLICATIONS

Dj Orthopedics LLC, OAdjuster, brochure, 2 pages, Jun. 2003.

Generation II USA Inc, Unloader Spirit, brochure, 4 pages, May 2001.

Office Action from U.S. Appl. No. 08/191,410 (DJORTH. 16CPCP2), Mailed Nov. 1, 1994.

* cited by examiner

OSTEOARTHRITIS BRACE

RELATED APPLICATION

This application claims priority to provisional application Ser. No. 60/564,563, filed on Apr. 21, 2004, the entire contents of which are hereby expressly incorporated by reference.

BACKGROUND OF THE INVENTION

1. Field of the Invention

The present invention relates to orthopedic braces.

2. Description of the Related Art

Osteoarthritis is a degenerative joint disease that causes chronic pain in an affected joint when the joint is statically or dynamically loaded. In an affected knee, osteoarthritis pain is often caused by an unbalanced loading on the medial or lateral compartment of the joint. Such unbalanced loading can generate increased pressure and reduce the clearance space between the condyles of the femur and tibial plateau. Increased pressure between the femoral and tibial surfaces in an affected compartment of the knee joint can cause cartilage degeneration. As cartilage degenerates, the osteoarthritis sufferer generally experiences increasing pain in the knee. Typically, the pain of osteoarthritis is more severe when dynamic pressure is applied to the joint.

Orthopedic knee braces are commonly applied to the leg to treat osteoarthritis of the knee. Such braces typically include an upper support portion, a lower support portion, and one or more hinge assemblies pivotally interconnecting the upper and lower support portions. The upper support portion is secured to the wearer's upper leg, while the lower support portion is secured to the wearer's lower leg. The hinge assembly (or assemblies) is located to a side of the wearer's knee. A condyle pad is typically located between each hinge assembly and the adjacent side of the knee.

Knee braces of the type described above serve to mitigate the negative consequences of osteoarthritis in the knee joint by applying a three-point bending load to the leg. A condyle pad of the brace applies a force to the side of the knee opposite the affected compartment. For example, a thickness of the adjacent condyle pad may be increased or the pad may be moved closer to the knee using a jackscrew or some other mechanism. The applied force generates resultant forces in the medial/lateral plane above and below the knee. The upper and lower support portions of the brace, respectively, apply these resultant forces on the side of the affected compartment. The applied force and the resultant forces comprise the three-point bending load on the leg. This load realigns the knee. By realigning the orientation of the knee joint, the knee brace reduces the load in the affected compartment of the knee, thereby lessening the pain and the other negative effects of osteoarthritis.

SUMMARY OF THE INVENTION

The preferred embodiments of the present osteoarthritis brace have several features, no single one of which is solely responsible for their desirable attributes. Without limiting the scope of this osteoarthritis brace as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include flesh containment, distribution of loads over a large portion of the wearer's flesh, elimination of pinch points and enhanced fitting capabilities.

One embodiment provides an osteoarthritis brace comprising a rigid upper cuff and a rigid lower cuff. At least one hinge pivotably couples the upper cuff to the lower cuff. At least a first semi-rigid cuff abuts a first surface of one of the upper and lower cuffs. The semi-rigid cuff has a larger profile than either of the upper and lower cuffs, such that the semi-rigid cuff is configured to distribute force over a larger area than either of the upper and lower cuffs.

Another embodiment provides an osteoarthritis brace comprising a rigid upper cuff and a rigid lower cuff. At least one hinge pivotably couples the upper cuff to the lower cuff. At least a first semi-rigid cuff abuts a first surface of one of the upper and lower cuffs. The semi-rigid cuff is not attached to the one of the upper and lower cuffs at a medial side thereof.

Another embodiment provides a method of treating an osteoarthritic knee. The method comprises the steps of applying a brace to a leg and applying pressure to a medial or lateral side of the knee using a force application assembly of the brace to alter the alignment of the knee. The force applied to the side of the knee is transferred to the opposite side of the knee and distributed over a large area of the wearer's leg, relative to the surface area of the rigid members of the brace, using at least one semi-rigid cuff.

BRIEF DESCRIPTION OF THE DRAWINGS

The preferred embodiments of the present osteoarthritis brace, illustrating its features, will now be discussed in detail. These embodiments depict the novel and non-obvious osteoarthritis brace shown in the accompanying drawings, which are for illustrative purposes only. These drawings include the following figures, in which like numerals indicate like parts.

DETAILED DESCRIPTION OF THE PREFERRED EMBODIMENT

As used herein, inner surface denotes a surface that faces the wearer when the brace is worn. As used herein, outer surface denotes a surface that faces away from the wearer when the brace is worn. Medial denotes a direction or location toward the vertical centerline of the wearer's body. Lateral denotes a direction or location away from the vertical centerline of the wearer's body.

Figure 1:
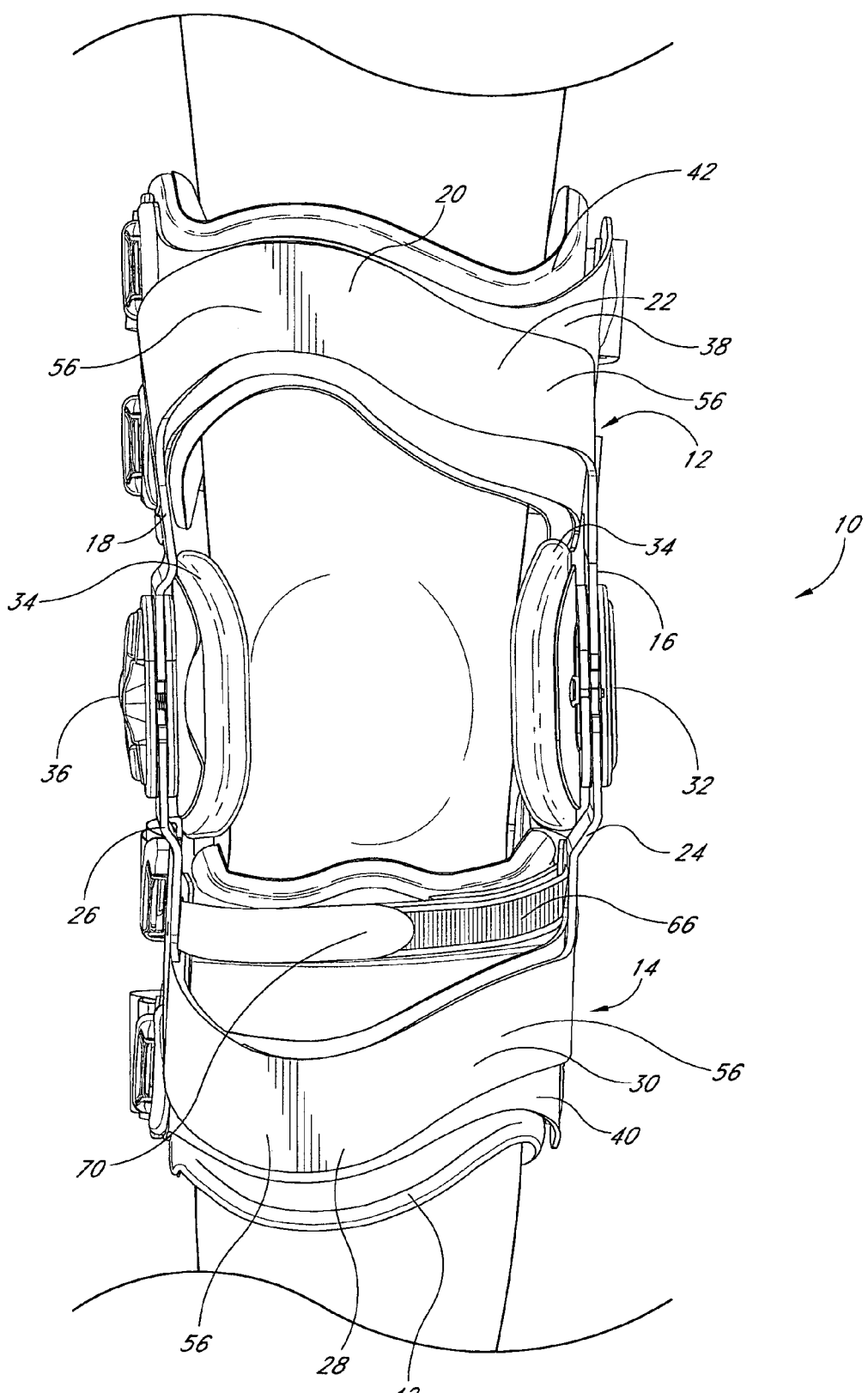
FIG. 1 is a front elevational view of one embodiment of the present osteoarthritis brace, illustrating the brace applied to a wearer's leg.

FIG. 1 illustrates one embodiment of the present osteoarthritis brace 10. The brace 10 illustrated in FIG. 1 is adapted to be worn on a right leg to treat medial compartment osteoarthritis. Those of skill in the art will appreciate that the principles of the illustrated brace 10 are adaptable to braces that are worn on either the right or left leg, and that are used to treat either medial or lateral compartment osteoarthritis. The particulars of the illustrated brace 10 are in no way intended to limit the scope of the present osteoarthritis brace 10.

The brace 10 comprises a rigid frame including an upper cuff 12 and a lower cuff 14. The upper cuff 12 includes a medial upright 16 and a lateral upright 18 that extend along medial and lateral portions, respectively, of the wearer's thigh. A transverse thigh member 20 extends between upper ends of the upper uprights 16, 18, and extends across the wearer's thigh when the brace 10 is worn. Rather than extending substantially straight across the wearer's thigh, a medial portion 22 of the transverse thigh member 20 swoops downward from approximately the middle of the wearer's thigh to the upper medial upright 16. This configuration provides greater comfort for the wearer, as described in more detail below.

The upper cuff 12 and lower cuff 14 of the brace 10 are preferably constructed of rigid materials, such as aluminum, steel or a composite material. However, those of skill in the art will appreciate that other rigid materials may be used instead.

The lower cuff 14 includes a medial upright 24 and a lateral upright 26 that extend along medial and lateral portions, respectively, of the wearer's calf. A transverse shin member 28 extends between lower ends of the uprights 26, 28, and extends across the wearer's shin when the brace 10 is worn. Rather than extending substantially straight across the wearer's shin, a medial portion 30 of the transverse calf member 28 swoops upward from approximately the middle of the wearer's shin to the lower medial upright 24. This configuration provides greater comfort for the wearer, as described in more detail below.

The upper and lower medial uprights 16, 24 are pivotably joined to one another by a medial hinge 32. The illustrated hinge 32 is bicentric. However, those of skill in the art will appreciate that other hinges, such as a monocentric hinge, could be used instead. A lateral surface of the medial hinge 32 may include a condyle pad 34 that is adapted to increase wearer comfort. The condyle pad 34 may include, for example, a resilient material, or a shape memory material.

The upper and lower lateral uprights 18, 26 are pivotably joined to one another by a lateral hinge 36. The illustrated hinge 36 is bicentric. However, those of skill in the art will appreciate that other hinges, such as a monocentric hinge, could be used instead. A medial surface of the lateral hinge 36 may include a condyle pad 34 that is adapted to increase wearer comfort. The condyle pad 34 may include, for example, a resilient material, or a shape memory material.

Figure 2:
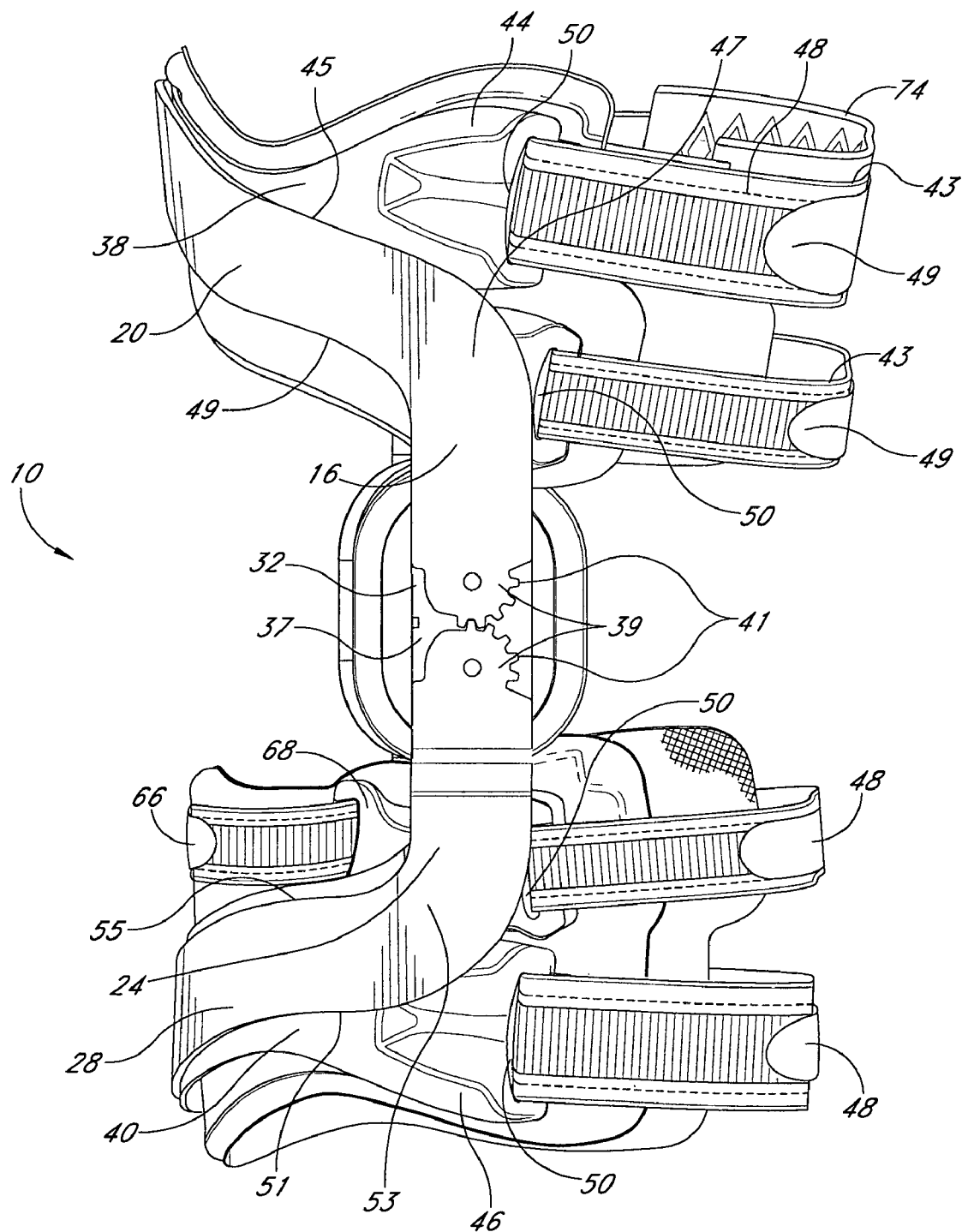
FIG. 2 is a right-side elevational view of the osteoarthritis brace of FIG. 1.

With reference to FIG. 2, the hinges 32, 36 include a hinge plate 37 and first and second gear members 39 pivotally connected to the hinge plate 37. Intermeshing gear teeth 41 couple the first and second gear members 39 to one another.

Figure 3:
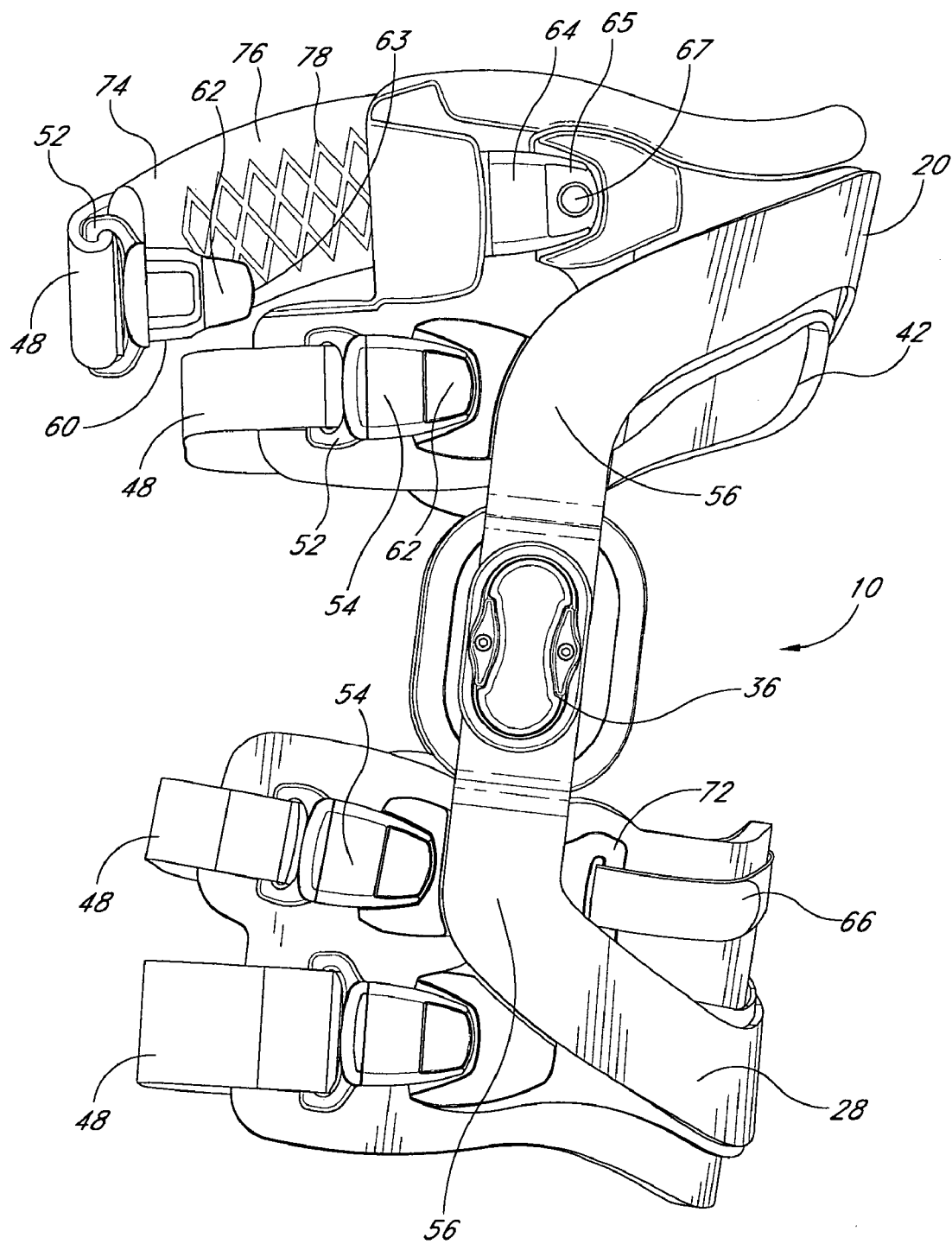
FIG. 3 is a left-side elevational view of the osteoarthritis brace of FIG. 1.

With reference to FIGS. 1 and 3, the lateral hinge 36 preferably includes a telescoping condyle pad 34 that allows the wearer to adjust a medial/lateral distance between the condyle pad 34 and the hinge 36. A hinge that is well-adapted for use as the lateral hinge 36 in the present brace 10 is illustrated in U.S. Pat. No. 6,752,775, issued on Jun. 22, 2004, the entire contents of which are hereby expressly incorporated by reference.

Figure 4:
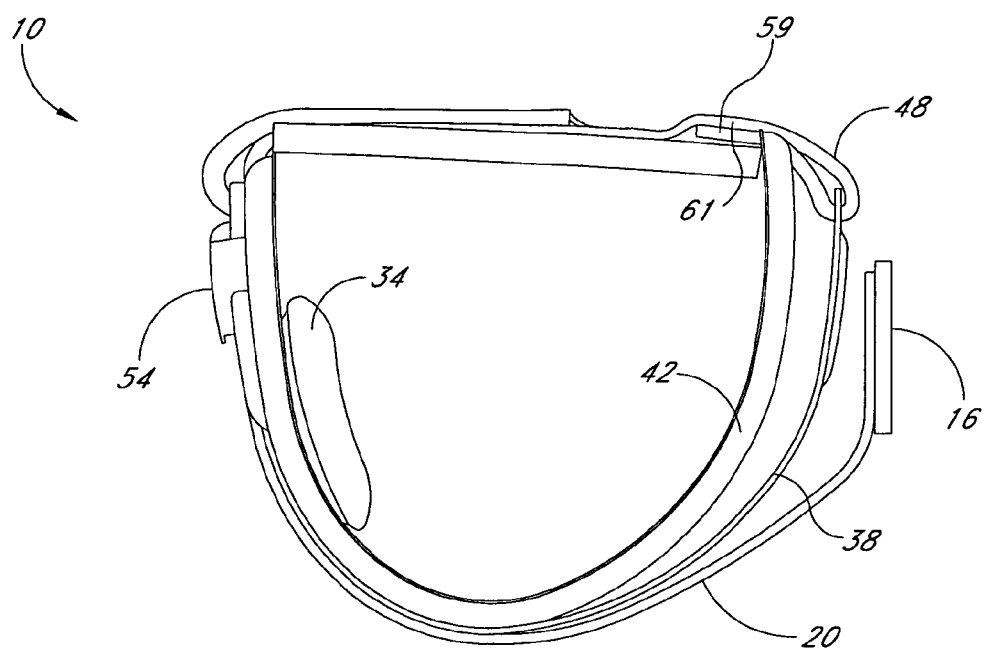
FIG. 4 is a top plan view of the osteoarthritis brace of FIG. 1.

With reference to FIGS. 1, 2 and 4, a semi-rigid cuff 38 abuts an inner surface of the transverse thigh member 20. Another semi-rigid cuff 40 similarly abuts an inner surface of the transverse calf member 28. In one embodiment, the semi-rigid cuffs 38, 40 are constructed of molded plastic, which is advantageously flexible and resilient. However, those of skill in the art will appreciate that other semi-rigid materials, such as certain types of rubbers, metals, or fiberglass may be used instead.

In the illustrated embodiment, and with further reference to FIGS. 1, 2 and 4, resilient padding material 42 abuts the inner surfaces of the semi-rigid cuffs 38, 40. The padding material 42 provides a comfortable interface between the semi-rigid cuffs 38, 40 and the wearer's leg. Those of skill in the art will appreciate that the padding 42 need not be provided.

In FIG. 4 the padding 42, semi-rigid cuff 38 and transverse thigh member 20 have been separated for clarity. (Note also that in FIG. 4, the lower half of the brace 10 has been omitted for clarity). However, when the brace 10 is in a resting state, the semi-rigid cuffs 38, 40 abut almost the entire posterior surfaces of the rigid cuffs 12, 14. Similarly, the padding 42 abuts almost the entire posterior surfaces of the semi-rigid cuffs 38, 40.

With reference to FIG. 2, the semi-rigid cuffs 38, 40 embody substantially larger profiles than the rigid transverse members 20, 28 that they abut. The medial portion 44 of the upper semi-rigid cuff 38 extends a considerable distance above an upper edge 45 of the transverse thigh member 20. The medial portion 44 also extends a considerable distance above and behind an upper portion 47 of the upper medial upright 16. The medial portion 44 also extends a considerable distance below a lower edge 49 of the transverse thigh member 20. This configuration creates a relatively large surface area on the inner surfaces of the upper semi-rigid cuff 38.

Likewise, the medial portion 46 of the lower semi-rigid cuff 40 extends a considerable distance below a lower edge 51 of the transverse thigh member 28. The medial portion 46 also extends a considerable distance below and behind a lower portion 53 of the lower medial upright 24. The medial portion 46 also extends a considerable distance above an upper edge 55 of the transverse thigh member 28. This configuration creates a relatively large surface area on the inner surfaces of the lower semi-rigid cuff 40.

As illustrated in FIGS. 2 and 3, a plurality of straps 48 extend across a posterior portion of the brace 10. When the brace 10 is worn, the straps 48 extend around the back of the wearer's leg to secure the brace 10 to the leg. In the illustrated embodiment, two straps 48 are provided to extend around the back of the wearer's thigh, and two straps 48 are provided to extend around the back of the wearer's calf. Those of skill in the art will appreciate that fewer or more straps could be provided.

With reference to FIGS. 2 and 3, in the illustrated embodiment the straps 48 include padded members 74 that are releasably secured at intermediate portions thereof. For clarity, a single padded member 74 is shown attached to the uppermost strap 48 only. Those of skill in the art will appreciate that each of the straps 48, or only select straps 48, could include padded members 74. Those of skill in the art will further appreciate that the padded members 74 need not be provided.

The padded members 74 may comprise, for example, a resilient material, or a shape memory material. Outer surfaces (not shown) of the padded members 74 include hook-and-loop material that releasably engages mating hook-and-loop material on inner surfaces (not shown) of the straps 48. Those of skill in the art will appreciate that alternative fastening devices, such as buttons or snaps, could be used instead of hook-and-loop. Those of skill in the art will further appreciate that the padded members 74 could be permanently attached to the straps 48, for example with stitching. With reference to FIG. 3, inner surfaces 76 of the padded members 74 may include a substance 78 that has a high coefficient of friction with respect to the wearer's skin. The substance 78 helps maintain the position of the brace 10 on the wearer's leg.

With reference to FIGS. 2 and 4, in one embodiment a first end 59 of each strap 48 engages a loop 50 on one side of the semi-rigid cuffs 38, 40 (in this case the medial side). The first end 59 of each strap 48 threads through one of the loops 50 and secures to an intermediate portion 61 of the inner surface of the same strap 48 using a suitable fastener, such as hook-and-loop. With reference to FIG. 3, a second end 49 (FIG. 2) of each strap 48 threads through a D-ring 52 of a quick-release buckle 54. Those of skill in the art will appreciate that other rings and buckles could be used instead. The second end 49 of each strap 48 similarly secures to an intermediate portion 43 of the same strap 48 using a suitable fastener, such as hook-and-loop.

With reference to FIG. 3, to engage each quick-release buckle 54 on each strap 48, the wearer slides a male component 60 of the buckle 54 into a female component 64 thereof. The male component 60 is attached to the D-ring 52 on the strap 48. The female component 64 is attached to one of the semi-rigid cuffs 38, 40.

The male component 60 may be molded integrally with the D-ring 52, as in the illustrated embodiment. Alternatively, the male component 60 may be formed as a separate piece and then secured to the D-ring 52. The female component 64 may be molded integrally with the one of the semi-rigid cuffs 38, 40. Alternatively, the female component 64 may be formed as a separate piece and then secured to the one of the semi-rigid cuffs 38, 40, as in the illustrated embodiment. In the illustrated embodiment, the female component 64 is pivotably secured to the one of the semi-rigid cuffs 38, 40 with a rivet 67. Those of skill in the art will appreciate that the female component 64 could be secured to the one of the semi-rigid cuffs 38, 40 in a variety of other ways, such as with alternative fasteners, e.g. screws or bolts, or adhesive.

A leading portion 62 of the male component 60 is substantially wedge-shaped, increasing in thickness away from a leading edge 63. The wedge-shaped leading portion 62 slides into a slot (not shown) in the female component 64. When completely inserted, the leading portion 62 snaps into an opening 65 of corresponding size and shape located on the female component 64. To disengage the quick-release buckle 54, the wearer presses on the leading portion 62 of the male component 60 to pop the leading portion 62 out of the opening 65. The wearer then slides the male component 60 away from the female component 64.

To secure the brace 10 to his or her leg, the wearer disengages each quick-release buckle 54, and places the brace 10 on his or her leg such that the padding 42 behind the transverse thigh and calf members 20, 28 abuts the anterior surfaces of the wearer's thigh and calf, respectively. The medial and lateral hinges 32, 36 are positioned adjacent the medial and lateral sides, respectively, of the wearer's knee. The wearer then secures each of the quick-release buckles 54 to the appropriate mating portion on the semi-rigid cuffs 38, 40. To tighten the straps 48, the wearer may loosen the ends of the straps 48 from the intermediate portions where they are secured, pull on the strap ends, and reattach the strap ends to the intermediate portions.

With reference to FIGS. 1, 2 and 3, in the illustrated embodiment a strap 66 extends across an anterior portion of the brace 10 just above the transverse calf member 28. With reference to FIG. 2, a first end (not shown) of the strap 66 threads through a medial loop 68 that is located adjacent the junction of the lower medial upright 24 and the transverse calf member 28. The first end of the strap 66 folds back on itself and secures to an intermediate portion of an inner surface of the strap 66 using a suitable fastener, such as hook-and-loop.

With reference to FIGS. 1 and 3, a second end 70 (FIG. 1) of the strap 66 engages a lateral loop 72 (FIG. 3) that is located adjacent the junction of the lower lateral upright 26 and the transverse calf member 28. The second end 70 of the strap 66 folds back on itself and secures to an intermediate portion of an outer surface of the strap 66 using a suitable fastener, such as hook-and-loop. The wearer may adjust the strap 66 by varying the position at which the first and second ends of the strap 66 engage the intermediate portions thereof. Those of skill in the art will appreciate that fewer or more straps 66 could be provided on the anterior portion of the brace 10.

In the illustrated embodiment, the loops 68, 72 are constructed of molded plastic. However, those of skill in the art will appreciate that the loops 68, 72 could be formed of a variety of other materials, such as metals. The medial loop 68 is formed separately from the semi-rigid cuff 40 and is pivotably secured to the lower cuff 14. The lateral loop 72 is formed integrally with the semi-rigid cuff 40. Those of skill in the art will appreciate that either of the loops 68, 72 could be formed separately from the semi-rigid cuff 40 or formed integrally with the semi-rigid cuff 40. In the illustrated embodiment, a rivet secures the medial loop 68 to the lower cuff 14. Those of skill in the art will appreciate that other methods of attachment could be used to secure either of the loops 68, 72 to the lower cuff 14 or to the semi-rigid cuff 40, such as fasteners (e.g. screws or bolts) or adhesives.

Figure 5:
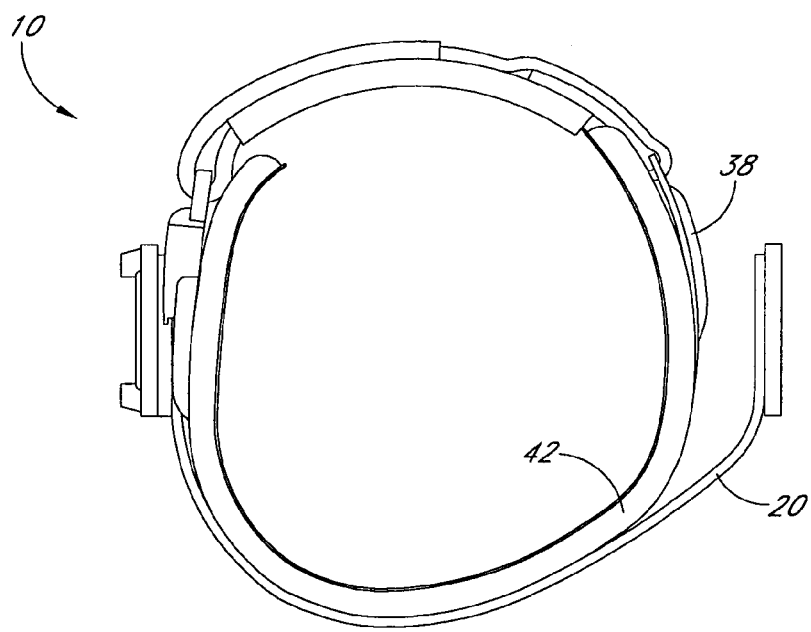
FIG. 5 is a top plan view of the osteoarthritis brace of FIG. 1, illustrating the capability of the semi-rigid cuff to separate from the rigid member.

In one embodiment, the semi-rigid cuffs 38, 40 are secured at only select locations on the lateral uprights 18, 26 and the transverse thigh and calf members 20, 28. With reference to FIGS. 1 and 3, these securing locations may be as indicated by the numerals 56. In this embodiment, the medial portions 44, 46 of the semi-rigid cuffs 38, 40 remain unattached to the medial uprights 16, 24 (FIGS. 1 and 2). Thus, when the straps 48 are properly tightened, the medial portions 44, 46 of the semi-rigid cuffs 38, 40 pull away from the inner surfaces of the transverse members 20, 28 and the medial uprights 16, 24, as shown in FIG. 5. (Note that in FIG. 5, the lower half of the brace 10 has been omitted for clarity). This configuration enables the padding 48 and the semi-rigid cuffs 38, 40 to closely conform to the shape of the wearer's leg, thereby contributing to a better fit for the brace 10.

In the illustrated embodiment, rivets (not shown) secure the semi-rigid cuffs 38, 40 to the rigid cuffs 12, 14 at the locations 56 indicated. Those of skill in the art will appreciate that alternative methods of attachment, besides rivets, could be used instead. For example, different fasteners, such as screws or bolts, or adhesives could be used. Those of skill in the art will further appreciate that the semi-rigid cuffs 38, 40 could be attached to the rigid cuffs 12, 14 at alternative and/or additional and/or fewer locations besides the locations 56 indicated.

As discussed above, the brace 10 illustrated herein is adapted to be worn on a right leg to treat medial compartment osteoarthritis. Those of skill in the art will appreciate that the principles of the illustrated brace 10 are adaptable to braces that are worn on either the right or left leg, and that are used to treat either medial or lateral compartment osteoarthritis. In such alternate braces, the configuration of certain components may be reversed. For example, the semi-rigid cuffs 38, 40 may be attached to the rigid cuffs 12, 14 at the medial side and at approximately a center between the lateral and medial sides.

Figure 6:
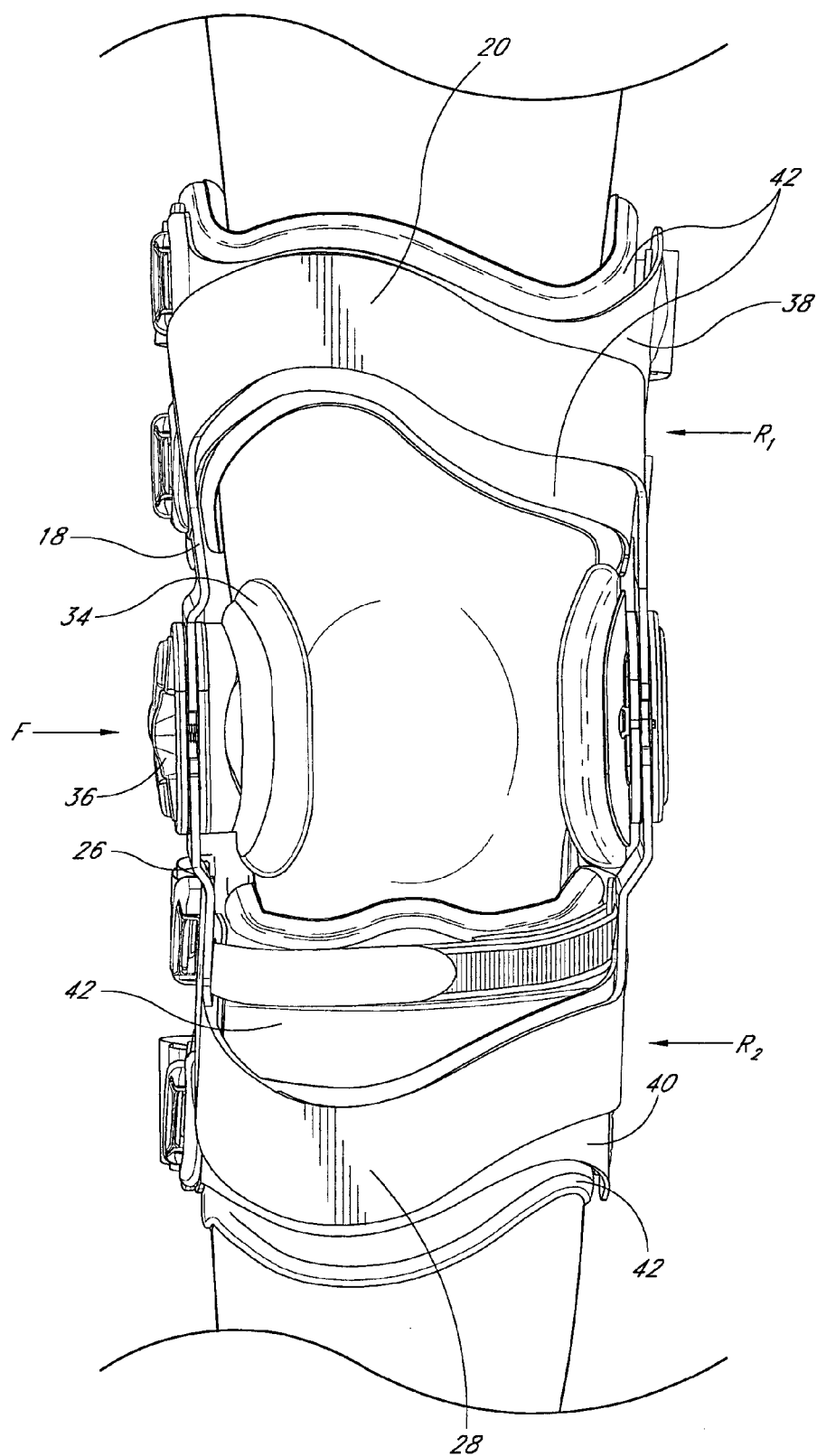
FIG. 6 is a front elevational view of the osteoarthritis brace of FIG. 1, illustrating the condyle pad extended toward the wearer's knee and applying a force thereto.

Once the brace 10 is properly applied, the wearer adjusts the lateral hinge 36 to move the telescoping condyle pad 34 away from the hinge 36. The condyle pad 34 thus applies a force F to the lateral side of the wearer's knee. The force F is transmitted through the rigid lateral uprights 18, 26 to the semi-rigid cuffs 38, 40. Because the wearer is snugly strapped into the brace 10, the force F generates reaction forces R1 and R2 on the medial side of the wearer's knee. The reaction forces R1 and R2 are applied to the upper medial upright 16 and the lower medial upright 24, near the medial portions 57 of the transverse members 20, 28, as shown in FIG. 6. The reaction forces are transmitted from the rigid members on the medial side of the knee to the adjacent semi-rigid cuffs 38, 40. Thus, the semi-rigid cuffs 38, 40 apply the forces R1 and R2 to the medial side of the wearer's thigh and calf.

The relatively large surface areas of the semi-rigid cuffs 38, 40 (as compared to the rigid cuffs 12, 14) creates several advantages for the present brace 10. For example, because the semi-rigid cuffs 38, 40 bear the reaction forces R1 and R2, they are able to distribute the reaction forces over a wider area than the relatively thin transverse members 20, 28 would be able to. Consequently, the semi-rigid cuffs 38, 40 increase wearer comfort.

Further, because the semi-rigid cuffs 38, 40, and not the transverse members 20, 28, bear the reaction forces R1 and R2, the transverse members 20, 28 are able to embody the swooping configuration described above. This configuration removes rigid brace material from the upper inner part of the wearer's thigh, where that material would otherwise have a tendency to create pinch points and generally interfere with the relative movement of the wearer's thighs.

The relatively large semi-rigid cuffs 38, 40 are also advantageously able to contain the wearer's flesh. This feature makes the present brace 10 particularly well adapted for use by wearers having greater girth in their legs. The flesh of such wearers tends to squeeze out around the relatively rigid brace components. The large semi-rigid cuffs provide greater flesh containment, which reduces the potential for pinching or for rubbing against the opposite leg.

In the embodiment wherein the semi-rigid cuffs 38, 40 are constructed of molded plastic, the cuffs 38, 40 can be advantageously molded with integrated features, such as the strap loops 50 shown in FIG. 2, the D-rings 52 shown in FIG. 3, the mating portions of a quick-release buckles 54, or other strap attachment features. The padding material 42, which may be thermoformed, is also well adapted to mate with molded plastic cuffs.

SCOPE OF THE INVENTION

The above presents a description of the best mode contemplated for carrying out the present osteoarthritis brace, and of the manner and process of making and using it, in such full, clear, concise, and exact terms as to enable any person skilled in the art to which it pertains to make and use this osteoarthritis brace. This osteoarthritis brace is, however, susceptible to modifications and alternate constructions from that discussed above that are fully equivalent. Consequently, this osteoarthritis brace is not limited to the particular embodiments disclosed. On the contrary, this osteoarthritis brace covers all modifications and alternate constructions coming within the spirit and scope of the osteoarthritis brace as generally expressed by the following claims, which particularly point out and distinctly claim the subject matter of the osteoarthritis brace.

What is claimed is:

1. An osteoarthritis brace configured to be applied to a wearer's leg to provide relief from pain caused by osteoarthritis, the brace comprising:
    a rigid cuff including a lateral upright configured to extend substantially vertically along a lateral side of the leg, a medial upright configured to extend substantially vertically along a medial side of the leg, and a transverse member extending between the uprights and configured to extend around at least a portion the leg;
    a semi-rigid cuff abutting an inner surface of the rigid cuff; and
    at least a first strap securable to the semi-rigid cuff and configured to extend around at least a portion the leg to secure the rigid cuff and the semi-rigid cuff to the leg;
    wherein the semi-rigid cuff is secured to the lateral upright and to the transverse member, but is not directly secured to the medial upright, such that tension in the strap tends to pull the semi-rigid cuff away from the medial upright.

2. The osteoarthritis brace of claim 1, wherein the rigid cuff is a first rigid cuff and further comprising a second rigid cuff.

3. The osteoarthritis brace of claim 2, further comprising a second semi-rigid cuff abutting an inner surface of the second rigid cuff.

4. The osteoarthritis brace of claim 2, further comprising at least one hinge pivotably coupling the first rigid cuff to the second rigid cuff.

5. The osteoarthritis brace of claim 4, further comprising at least one condyle pad.

6. The osteoarthritis brace of claim 4, wherein the condyle pad is located adjacent the hinge, and is configured to apply a force to a knee of the wearer.

7. The osteoarthritis brace of claim 4, wherein the distance between the condyle pad and the hinge is adjustable.

8. The osteoarthritis brace of claim 1, wherein the semi-rigid cuff is substantially coextensive with the rigid cuff, but the semi-rigid cuff defines a larger surface area than the rigid cuff.

9. The osteoarthritis brace of claim 1, further comprising resilient padding material abutting an inner surface of the semi-rigid cuff.

10. The osteoarthritis brace of claim 1, wherein the semi-rigid cuff is constructed from at least one of plastic, rubber, metal, and fiberglass.

11. The osteoarthritis brace of claim 1, wherein the semi-rigid cuff includes at least one of a first portion of a quick-release buckle.

12. The osteoarthritis brace of claim 11, wherein the first portion of the quick-release buckle is formed integrally with the semi-rigid cuff.

13. An osteoarthritis brace configured to be applied to a wearer's leg to provide relief from pain caused by osteoarthritis, the brace comprising:
    a rigid cuff including a lateral upright configured to extend substantially vertically along a lateral side of the leg, a medial upright configured to extend substantially vertically along a medial side of the leg, and a transverse member extending between the uprights and configured to extend around at least a portion the leg;
    a semi-rigid cuff abutting an inner surface of the rigid cuff; and at least a first strap securable to the semi-rigid cuff and configured to extend around at least a portion the leg to secure the rigid cuff and the semi-rigid cuff to the leg;

wherein the semi-rigid cuff is secured to the medial upright and to the transverse member, but is not directly secured to the lateral upright, such that tension in the strap tends to pull the semi-rigid cuff away from the lateral upright.

* * * * *